(12) United States Patent
Rinner et al.

(10) Patent No.: US 9,351,768 B2
(45) Date of Patent: May 31, 2016

(54) BONE SCREW RETENTION IN A SPINAL IMPLANT

(75) Inventors: James A. Rinner, Franksville, WI (US); Daniel Predick, Chicago, IL (US); Michael S. Butler, St. Charles, IL (US)

(73) Assignee: Life Spine, Inc., Huntley, IL (US)

( * ) Notice: Subject to any disclaimer, the term of this patent is extended or adjusted under 35 U.S.C. 154(b) by 284 days.

(21) Appl. No.: 13/593,862

(22) Filed: Aug. 24, 2012

(65) Prior Publication Data

US 2013/0053887 A1 Feb. 28, 2013

Related U.S. Application Data

(60) Provisional application No. 61/527,667, filed on Aug. 26, 2011.

(51) Int. Cl.
*A61B 17/70* (2006.01)
*A61B 17/80* (2006.01)

(52) U.S. Cl.
CPC ......... *A61B 17/7059* (2013.01); *A61B 17/8042* (2013.01)

(58) Field of Classification Search
CPC ........... A61B 17/8033; A61B 17/8042; A61B 17/8047; A61B 17/8052; A61B 17/8057; A61B 17/58; A61B 17/7058; A61B 17/7059; A61B 17/80; A61B 17/8004; A61B 17/8009; A61B 17/8014; A61B 17/8019; A61B 17/8023; A61B 17/8028; A61B 17/8061; A61B 17/8066; A61B 17/8071; A61B 17/8076; A61B 17/809
USPC ............... 606/280, 70, 71, 281–299
See application file for complete search history.

(56) References Cited

U.S. PATENT DOCUMENTS

| | | | | |
|---|---|---|---|---|
| 6,261,291 B1 * | 7/2001 | Talaber | .................. | A61B 17/80 606/281 |
| 6,524,315 B1 * | 2/2003 | Selvitelli | ............ | A61B 17/7044 606/278 |
| 6,547,790 B2 * | 4/2003 | Harkey, III | ......... | A61B 17/7044 606/250 |
| 6,602,255 B1 * | 8/2003 | Campbell | .......... | A61B 17/8042 606/290 |
| 6,695,846 B2 * | 2/2004 | Richelsoph | ........ | A61B 17/8042 606/290 |
| 7,025,769 B1 * | 4/2006 | Ferree | ................ | A61B 17/8042 606/281 |
| 7,481,811 B2 * | 1/2009 | Suh | ..................... | A61B 17/8042 606/289 |
| 7,524,325 B2 * | 4/2009 | Khalili | ............... | A61B 17/7059 606/290 |
| 7,651,517 B2 * | 1/2010 | Konieczynski | .... | A61B 17/8038 606/287 |
| 7,740,649 B2 * | 6/2010 | Mosca | ................ | A61B 17/1615 606/280 |
| 7,857,839 B2 * | 12/2010 | Duong | ............... | A61B 17/8047 606/280 |
| 7,887,547 B2 * | 2/2011 | Campbell | .......... | A61B 17/8042 606/104 |

(Continued)

*Primary Examiner* — Pedro Philogene
*Assistant Examiner* — Lynnsy Summitt
(74) *Attorney, Agent, or Firm* — Foley & Lardner LLP

(57) ABSTRACT

A spinal implant has a mechanism for inhibiting a bone screw used in attaching the spinal implant to the spine from backing out from the spinal implant once the bone screw has been received in the spinal implant. The spinal implant has a bone screw bore defining a bore wall in which is disposed a resilient closed curve band or ring. The resilient closed curve band has a plurality of resilient segments that extend into the bore. Each one of the plurality of resilient segments form a spring that allows a head of a bone screw to ingress there through but prevents the head of the bone screw from egress there from. The resilient closed curve band forms a retention ring that is received in one or more slots, channels, grooves or the like in the bore hole wall. The plurality of resilient segments are formed as arcs, curves and/or configured arcs/curves that extend radially inward from outer arced or curved portions of the retention ring.

9 Claims, 5 Drawing Sheets

(56) References Cited

U.S. PATENT DOCUMENTS

| | | | | |
|---|---|---|---|---|
| 7,909,859 B2* | 3/2011 | Mosca | A61B 17/1615 606/289 |
| 7,909,860 B2* | 3/2011 | Rathbun | A61B 17/1728 606/280 |
| 7,972,366 B2* | 7/2011 | Richelsoph | A61B 17/7059 606/290 |
| 8,043,346 B2* | 10/2011 | Markworth | A61B 17/7059 606/294 |
| 8,057,522 B2* | 11/2011 | Rothman | A61B 17/8042 606/289 |
| RE43,008 E* | 12/2011 | Talaber | A61B 17/80 606/289 |
| 8,211,154 B2* | 7/2012 | Fisher | A61B 17/8047 606/289 |
| 8,216,285 B2* | 7/2012 | Markworth | A61B 17/7059 606/294 |
| 8,262,659 B2* | 9/2012 | Ryan | A61B 17/7059 606/71 |
| 8,287,550 B2* | 10/2012 | Campbell | A61B 17/8042 606/104 |
| 8,343,194 B2* | 1/2013 | Aflatoon | A61B 17/7059 606/280 |
| 8,343,195 B2* | 1/2013 | Rathbun | A61B 17/1728 606/104 |
| 8,353,939 B2* | 1/2013 | Anderson | A61B 17/8042 606/289 |
| 8,454,666 B2* | 6/2013 | Tornier | A61B 17/8042 606/289 |
| 8,470,006 B2* | 6/2013 | Paul | A61B 17/7059 606/280 |
| 8,496,691 B2* | 7/2013 | Blain | A61B 17/7059 606/288 |
| 8,496,693 B2* | 7/2013 | Robinson | A61B 17/8042 606/289 |
| 8,500,737 B2* | 8/2013 | Richelsoph | A61B 17/8042 606/280 |
| 8,535,354 B2* | 9/2013 | Cummins | A61B 17/7059 411/398 |
| 8,551,144 B2* | 10/2013 | Youssef | A61B 17/8009 606/282 |
| 8,562,656 B2* | 10/2013 | Humphreys | A61B 17/7059 606/289 |
| 8,574,270 B2* | 11/2013 | Hess | A61B 17/7059 606/282 |
| 8,591,556 B2* | 11/2013 | Hansell | A61B 17/8052 606/289 |
| 8,613,761 B2* | 12/2013 | Lindemann | A61B 17/7059 606/289 |
| 8,623,019 B2* | 1/2014 | Perrow | A61B 17/1671 606/279 |
| 8,668,723 B2* | 3/2014 | Altarac | A61B 17/7059 606/290 |
| 8,696,721 B2* | 4/2014 | Blain | A61B 17/7059 606/290 |
| 8,702,762 B2* | 4/2014 | Jacene | A61B 17/8047 606/281 |
| 8,702,764 B2* | 4/2014 | Rusch | A61B 17/8047 606/289 |
| 8,734,495 B2* | 5/2014 | Black | A61B 17/7059 606/290 |
| 8,734,496 B2* | 5/2014 | Campbell | A61B 17/8042 606/289 |
| 8,747,441 B2* | 6/2014 | Konieczynski | A61B 17/8042 606/280 |
| 8,758,347 B2* | 6/2014 | Weiner | A61B 17/8009 606/282 |
| 2004/0030338 A1* | 2/2004 | Paul | A61B 17/7059 606/295 |
| 2005/0021032 A1* | 1/2005 | Koo | A61B 17/7059 606/295 |
| 2005/0049595 A1* | 3/2005 | Suh | A61B 17/7059 606/71 |
| 2005/0192577 A1* | 9/2005 | Mosca | A61B 17/1615 606/86 B |
| 2006/0235403 A1* | 10/2006 | Blain | A61B 17/7059 606/249 |
| 2007/0123884 A1* | 5/2007 | Abdou | A61B 17/8042 606/279 |
| 2009/0012571 A1* | 1/2009 | Perrow | A61B 17/1671 606/280 |
| 2009/0182383 A1* | 7/2009 | Prybyla | A61B 17/8047 606/280 |
| 2010/0121383 A1* | 5/2010 | Stanaford | A61B 17/8042 606/280 |
| 2012/0065682 A1* | 3/2012 | Duong | A61B 17/8047 606/246 |
| 2012/0065690 A1* | 3/2012 | Perrow | A61B 17/7059 606/294 |
| 2012/0191141 A1* | 7/2012 | Costabile | A61B 17/8042 606/295 |
| 2012/0283782 A1* | 11/2012 | Ryan | A61B 17/7059 606/279 |
| 2013/0184767 A1* | 7/2013 | Kaufman | A61B 17/8047 606/290 |
| 2013/0190825 A1* | 7/2013 | Perrow | A61B 17/8042 606/281 |
| 2013/0197588 A1* | 8/2013 | Abdou | A61B 17/8042 606/279 |
| 2013/0304132 A1* | 11/2013 | Heilman | A61B 17/8047 606/281 |
| 2014/0039564 A1* | 2/2014 | Hess | A61B 17/7059 606/294 |
| 2014/0128924 A1* | 5/2014 | Perrow | A61B 17/7059 606/287 |

* cited by examiner

BONE SCREW RETENTION IN A SPINAL IMPLANT

CROSS REFERENCE TO RELATED APPLICATIONS

This non-provisional patent application claims the benefit of and/or priority under 35 U.S.C. §119(e) to U.S. Provisional Patent Application Ser. No. 61/527,667 filed Aug. 26, 2011, entitled "Bone Screw Retention In A Spinal Implant" the entire contents of which is specifically incorporated herein by reference.

BACKGROUND OF THE INVENTION

1. Field of the Invention

The present invention relates to spine fixation components, constructs and assemblies and, more particularly, to mechanisms for retaining bone screws relative to a spinal implant once implanted.

2. Background Information

Spinal orthopedic assemblies and constructs such as spine plates, spinal bone screw assemblies for spinal rods and other devices have made a profound contribution to the correction of spinal deformities, accidents and other problems in the cervical as well as thoracic, lumbar and sacral spine. These and other spinal devices are typically fixed to vertebrae using vertebral bone screws. Vertebral bone screws are specially designed and manufactured bone screws that are placed into the bone of a vertebra. Vertebral bone screws placed in the vertebra offer superior strength and pull-out resistance as compared to other forms of fixation in spine surgery. The ability to achieve vertebral fixation has allowed surgeons to obtain more secure fixation of the spinal components involved, which permits more powerful correction of spine problems and reported better clinical outcomes.

Bone screws thus allow solid attachment of various types of spinal implants such as spine plates and spine rod holders to vertebrae of the spine. The spinal implants are thus configured to receive and retain one or more bone screws. Once implanted, it is important that a bone screw not back out. In this regard, various anti back out devices have been developed that attempt to limit and/or prevent bone screw back out. For example, anti back-out devices have been developed that attach into the drive socket of the bone screw and to the spinal implant. Those and other anti back out devices, however, suffer from deficiencies that make them less than ideal.

In view of the above, there is a need for an improved bone screw retention mechanism for spinal implants.

SUMMARY OF THE INVENTION

The present invention is a spinal implant having a mechanism for inhibiting a bone screw from backing out from the spinal implant once the bone screw has been received in the spinal implant.

The spinal implant has a bone screw bore defining a bore wall in which is disposed a resilient closed curve band or ring. The resilient closed curve band has a plurality of resilient sections or portions that extend into the bore. Each one of the plurality of resilient sections that extend into the bore form a spring that allows a head of a bone screw to ingress there through but prevents the head of the bone screw from egress there from.

The resilient closed curve band forms a retention ring that is received in one or more channels, grooves or the like in the bore hole wall. The plurality of resilient sections are formed as arcs, curves and/or configured arcs/curves that extend radially inward from outer arced or curved portions of the retention ring.

The resilient retention ring is thus configured to provide interaction with the bone screw head as the bone screw head passes through the resilient retention ring. Additionally, the bone screw head may be configured to provide interaction with the resilient retention ring as the bone screw head passes through the resilient retention ring. The bone screw head may moreover by configured to aid in retention of the bone screw by the resilient retention ring once the bone screw is properly installed.

The resilient retention ring is preferably, but not necessarily, a continuous body and preferably, but not necessarily, made from a nickel titanium alloy.

Moreover, the resilient retention ring is preferably, but not necessarily, formed of a resilient wire.

The spinal implant may be any spinal implant that utilizes a bone screw.

BRIEF DESCRIPTION OF THE DRAWINGS

The above mentioned and other features, advantages and objects of this invention, and the manner of attaining them, will become apparent and the invention itself will be better understood by reference to the following description of embodiments of the invention taken in conjunction with the accompanying drawings, wherein.

Like or similar reference numerals indicate the same or similar parts throughout the several figures.

A description of the features, functions and/or configuration of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF THE INVENTION

Figure 1:
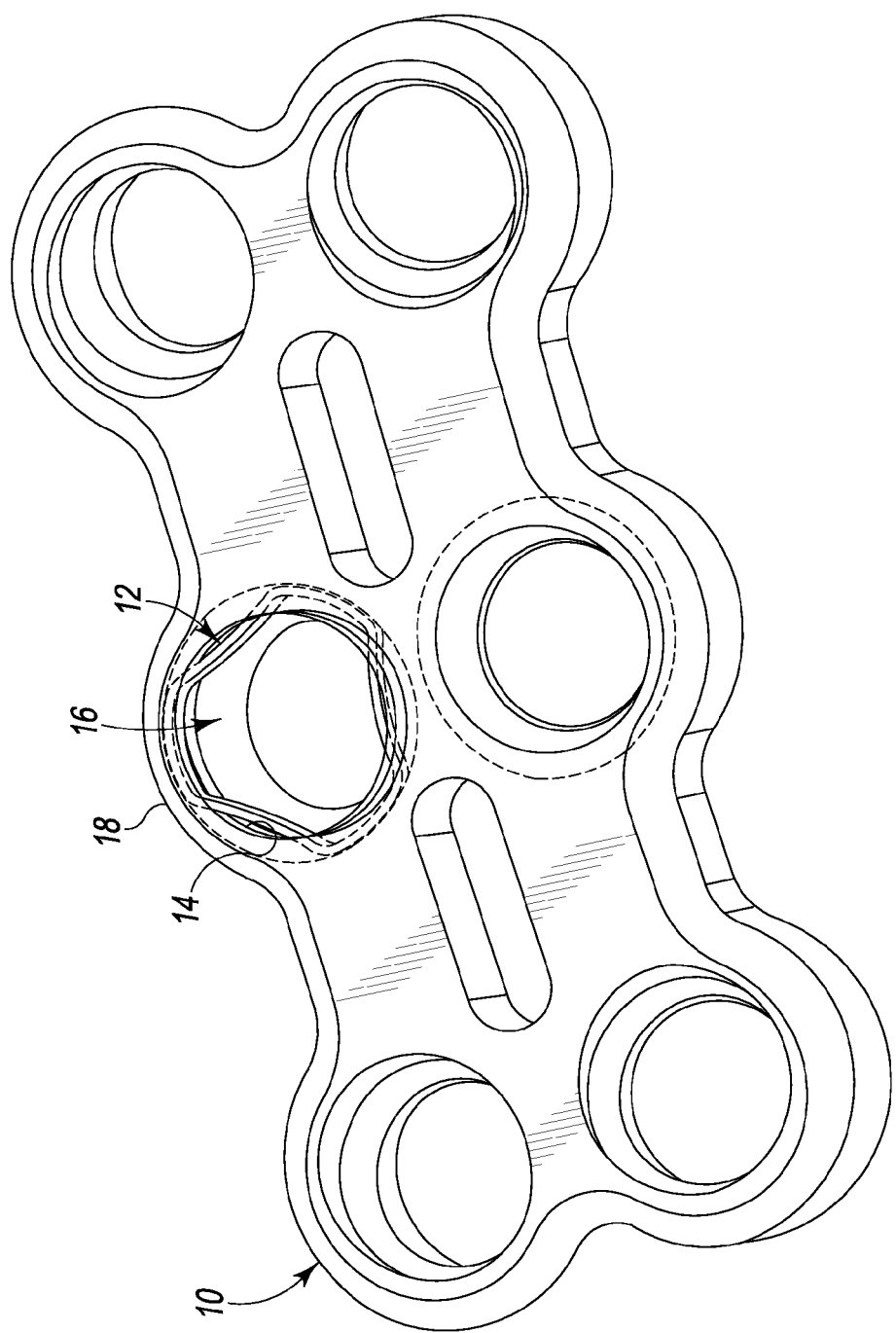
FIG. 1 is an isometric view of a spinal implant fashioned as a plate incorporating a bone screw retention mechanism in accordance with the present principles.

Referring to FIG. 1 there is depicted an exemplary spine plate 10 presented as an exemplary spinal implant incorporating the present invention. The spine plate 10 includes several bone screw bosses or seats of which a middle bone screw boss/seat 18, having a bone screw bore or hole 16 defining a bore or hole wall, has a resilient retention ring, band or structure 12 situated in a slot, channel, groove, undercut or the like 14 in the bore hole wall, the resilient retention ring 12 being one exemplary embodiment of a retention ring in accordance with the present principles. It should be appreciated that while a single channel 14 is shown and described herein, multiple, channels may be provided in order to hold the resilient retention ring 12 depending on the configuration of the resilient retention ring 12. The channel 14 is preferably, but not necessarily disposed about an upper portion of the bore wall/ middle bone screw seat 18, the resilient retention ring 12 and the retention channel 14 forming a bone screw retention mechanism or structure. The resilient retention ring 12 is shaped to allow a threaded shank and a head of a bone screw (not shown) to pass through and thus into the bone screw bore 16 but thereafter prevent and/or inhibit the bone screw from backing out from the bone screw bore 16. The resilient retention ring 12 thus keeps the head of the bone screw within the bone screw bore of the implant.

Figure 2:
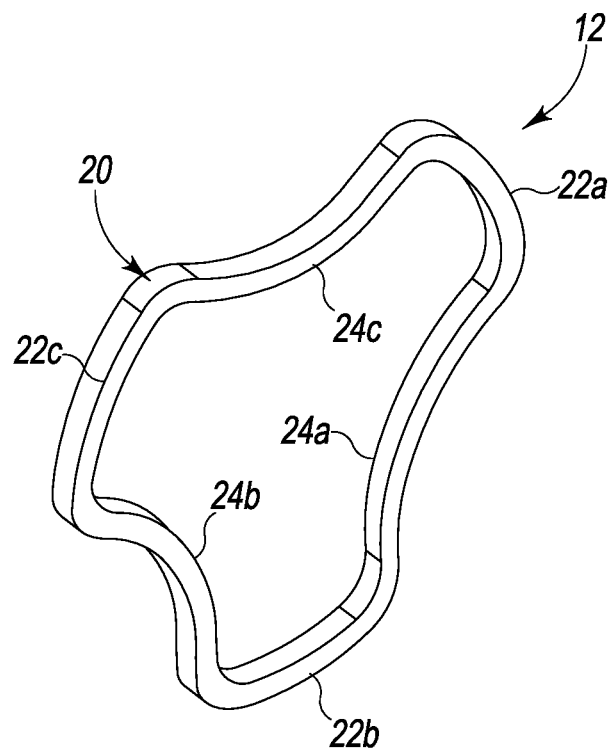
FIG. 2 is an isometric view of an embodiment of a resilient retention ring of the bone screw retention mechanism of FIG. 1.

The resilient retention ring 12 is particularly shaped to provide several springs or resilient segment, portions or sections that, when installed in the bone screw bore channel(s), extend radially into the bone screw bore 16. Referring additionally to FIG. 2, the retention ring 12 is particularly shown. The retention ring 12 is formed by a preferably, but not necessarily, continuous closed curve ring or body 20 of a biocompatible resilient, and/or elastic material so as to provide a spring force when deformed. Rather than being continuous, the retention ring may be formed of a plurality of arced or curved segments, portions or sections that are retained in one or more grooves, channels, slots undercuts or the like that extend radially into the bone screw bore. Preferably, the retention ring 12 is formed of nitinol (a nickel titanium alloy) since nitinol exhibit shape memory, resiliency and elasticity.

In this particular embodiment, the body 20 of the retention ring 12 has three segments, portions or sections formed as arcs, waves or curves 24a, 24b, 24c each one of which defines or creates a spring or spring-like structure that extends radially into the bone screw bore of the spinal implant, while connecting portions, segments or sections 22a, 22b, 22c extend into the retention channel 14 of the bone screw bore. In this manner, the retention ring 12 is retained in the retention channel 14 while the springs 24a, 24b, 24c extend radially into the bone screw bore. The springs 24a, 24b, 24c are preferably, but not necessarily, evenly spaced about the ring 12 and create an opening in the middle or proximate middle thereof in order to allow the introduction of a bone screw. While the springs 24a, 24b, 24c are shown as having the same shape and extending radially into the bore hole the same distance, the springs may not have the same shape nor do they all necessarily extend the same distance into the bore hole. As the bone screw is placed into the bone screw bore, the threaded shank of the bone screw fits through the opening in the middle of the springs 24a, 24b, 24c while the bone screw head, because of its size, must flex, flatten or push the springs 24a, 24b, 24c radially outward thereby allowing the bone screw head to move past the springs and into the bone screw bore. Typical bone screw heads have a rounded underside that spreads the springs 24a, 24b, 24c radially outward during insertion. Once the bone screw head has been inserted past the springs 24a, 24b, 24c, the springs 24a, 24b, 24c flex back to their original shape to extend into the bone screw bore. Since the bone screw head 30 (see e.g. FIG. 3) is typically flat or substantially flat, the springs 24a, 24b, 24c prevent the egress of the bone screw head and thus the bone screw. The opening between the springs 24a, 24b, 24c allows the insertion of a tool (not shown) into a configured socket of the bone screw head 30 (see e.g. FIG. 3) in order to appropriately screw the bone screw into a spinal bone.

Figure 3:
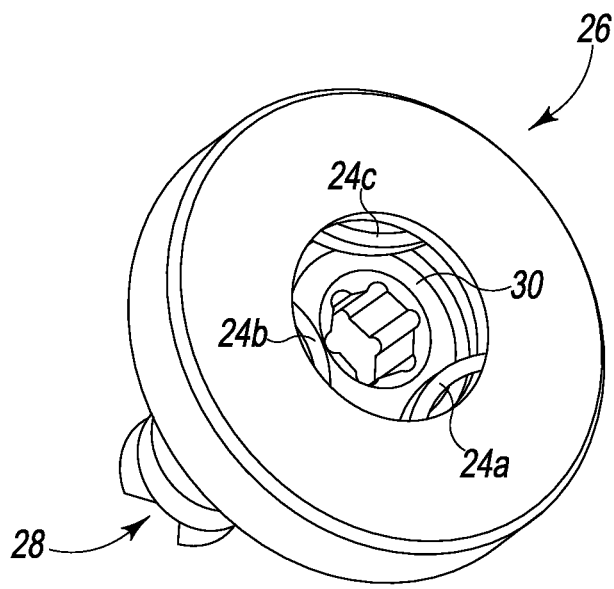
FIG. 3 is an isometric view of a mock up a bone screw hole of a spinal implant having the present bone screw retention mechanism and using the resilient retention ring of FIG. 2.

FIG. 3, illustrating a mock up 26 of a bone screw bore of a spinal implant incorporating the present bone screw retention mechanism, illustrating a bone screw 28 captured by the present bone screw retention mechanism. The springs 24a, 24b, 24c elastically deform in the radial direction in order to spread outwardly and into the retention channel when the head 30 of the bone screw 28 is forced down and between the springs 24a, 24b, 24c. Interaction and/or functionality between the bone screw head 30 and the springs 24a, 24b, 24c of the ring 12 may be enabled, provided and/or controlled through appropriate interface geometry of the bone screw head and/or the springs. In FIG. 3 the radiused underside of the head 30 of the bone screw 28 interacts with the springs 24a, 24b, 24c of the ring 12 to spread the springs 24a, 24b, 24c open. Other geometries, configurations, features, structure and/or structures of the bone screw/bone screw head and/or springs are contemplated. Thereafter, when the head 30 clears the springs 24a, 24b, 24c, the springs 24a, 24b, 24c elastically spring outward to block egress of the head 30 from the bone screw bore. The springs 24a, 24b, 24c extend over and/or about the top of the head 30 of the bone screw bore. The interaction and/or functionality between the top of the head 30 and the springs 24a, 24b, 24c may be enabled, provided and/or controlled through appropriate interface geometry of the top of the bone screw head and/or the springs. In FIG. 3, since the top of the head 30 is flat it cannot spread the curved springs 24a, 24b, 24c and thus is captured in the bone screw bore. Other geometries and/or configurations of the top of the bone screw head and/or springs are contemplated.

Figure 4:
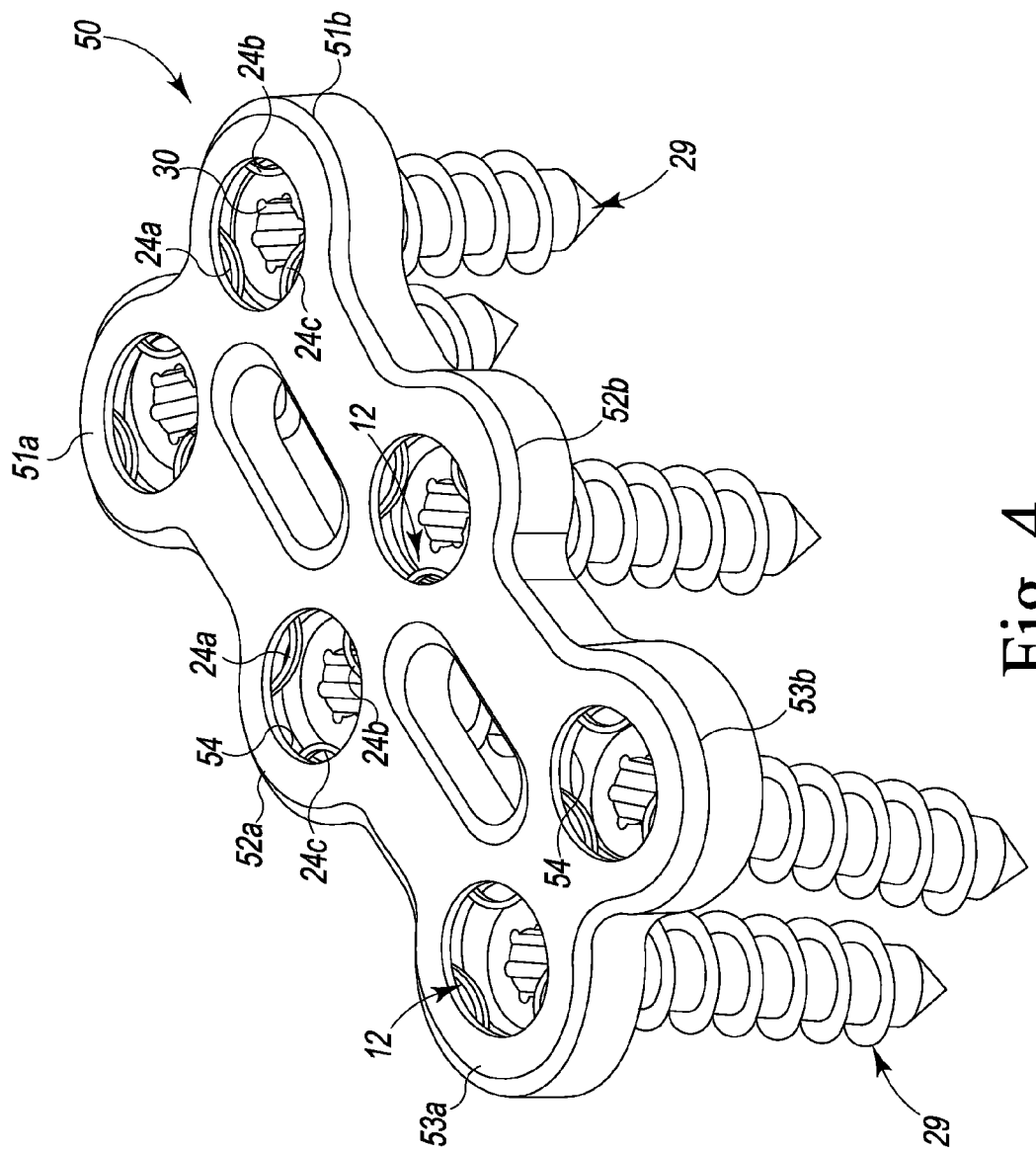
FIG. 4 is an isometric view of a two level static spine plate incorporating the present bone screw retention mechanism using the resilient retention ring of FIG. 2.
Figure 5:
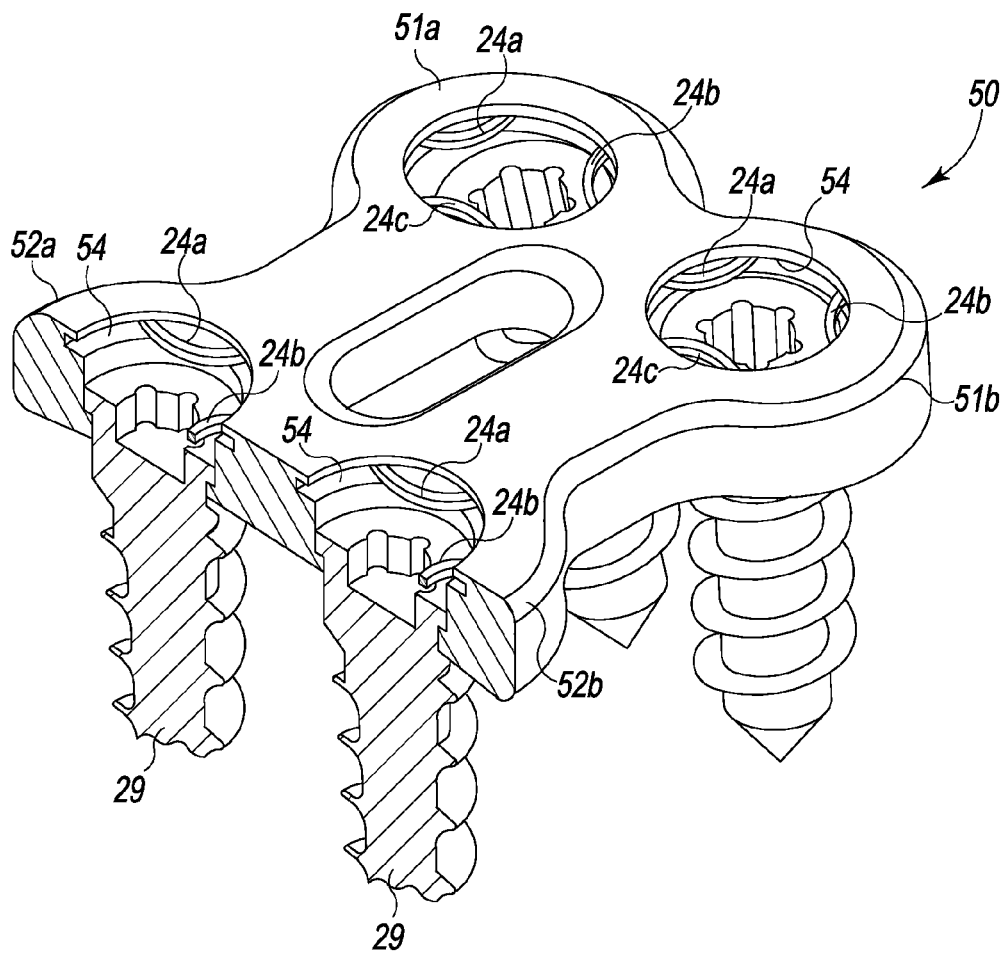
FIG. 5 is an enlarged isometric view of a sectioned portion of the spine plate of FIG. 4 particularly showing two bone screw holes or bores thereof in sectional illustrating the present bone screw retention mechanism.

Referring to FIGS. 4 and 5, there is depicted an exemplary two level (2-L) spine plate (implant) 50 utilizing the present bone screw retention mechanism/structure for each bone screw boss/seat. As shown, the spine plate 50 has a first end pair of bone screw bosses/seats 51a, 51b, a second end pair of bone screw bosses/seats 53a, 53b and a middle pair of bone screw bosses/seats 52a, 52b between the first and second end bosses/seats. Each bone screw boss/seat defines a bone screw bore have a retention channel 54 therein and a retention ring 12 trapped in the retention channel 54. Bone screws 29 are shown retained in the bone screw bosses/seats. FIG. 5 particularly shows how the retention ring 12 is captured or trapped in the retention channel 54 while the springs 24a, 24bm 24c of the retention ring 12 extend into the bone screw bore and over the bone screw head.

Figure 6:
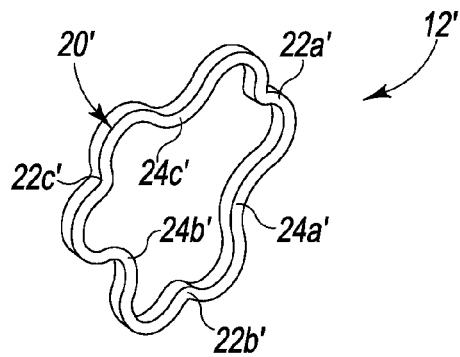
FIG. 6 is an isometric view of another embodiment of a resilient retention ring for the present bone screw retention mechanism.

Referring to FIG. 6 there is shown another embodiment of a retention ring 12' for the present bone screw retention mechanism/structure. The retention ring 12' is shaped to provide several springs that extend radially into the bone screw bore. The retention ring 12' is formed by a preferably, but not necessarily, continuous ring or body 20' of a biocompatible and elastic material so as to provide a spring force when deformed. Preferably, the retention ring 12' is formed of nitinol (a nickel titanium alloy) since nitinol/nitinol alloys exhibit shape memory and elasticity. The body 20' of the retention ring 12' has three waves or curves 24a', 24b', 24c' that each define a spring which extends radially into the bone screw bore of the spinal implant, while the connecting portions 22a', 22b', 22c' extend into the retention channel of the bone screw bore. In this manner, the retention ring 12' is thus trapped or retained in the retention channel while the springs 24a', 24b', 24c' extend into the bone screw bore. The springs 24a', 24b', 24c' are preferably, but not necessarily, evenly spaced about the ring 12' and create an opening in the middle thereof in order to allow the introduction of a bone screw. The other features, structures, and/or variations discussed with regard to the retention ring 12 not discussed in this paragraph applies to the retention ring 12' and is hereby incorporated herein by reference.

Figure 7:
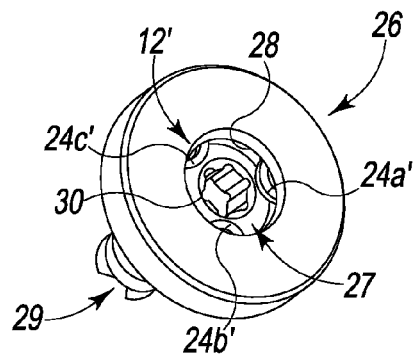
FIG. 7 is an isometric view of another mock up a bone screw hole of a spinal implant having the present bone screw retention mechanism using the resilient retention ring of FIG. 6.

FIG. 7 illustrates another mock up 26 of a bone screw bore of a spinal implant incorporating the present bone screw retention mechanism having a bone screw 29 captured by the present bone screw retention mechanism. The springs 24a', 24b', 24c' elastically deform in the radial direction in order to spread outwardly and into the retention channel when the head of the bone screw 29 is forced down and between the springs 24a', 24b', 24c'. Interaction and/or functionality between the bone screw head 30 and the springs 24a', 24b', 24c' of the ring 12' may be enabled, provided and/or controlled through appropriate interface geometry of the bone screw head and/or the springs. In FIG. 7 the radiused underside of the head 30 of the bone screw 29 interacts with the springs 24a', 24b', 24c' of the ring 12' to spread the springs 24a', 24b', 24c' open. Other geometries, configurations, features, structure and/or structures of the bone screw/bone screw head and/or springs are contemplated. Thereafter, when the head clears the springs 24a', 24b', 24c', the springs 24a', 24b', 24c' elastically spring outward to block egress of the head from the bone screw bore. Particularly, the springs 24a', 24b', 24c' extend over and/or about the top of the head of the bone screw bore. The interaction and/or functionality between the top of the head 30 and the springs 24a', 24b', 24c' may be enabled, provided and/or controlled through appropriate interface geometry of the top of the bone screw head and/or the springs. In FIG. 7, since the top of the head is flat, it cannot spread the curved springs 24a', 24b', 24c' and thus is captured in the bone screw bore. Other geometries and/or configurations of the top of the bone screw head and/or springs are contemplated.

Figure 8:
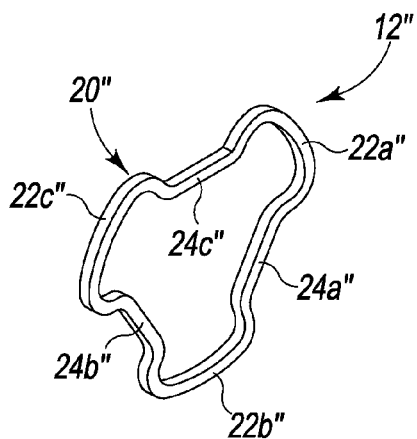
FIG. 8 is an isometric view of another embodiment of a resilient retention ring for the present bone screw retention mechanism.

Referring to FIG. 8 there is shown another embodiment of a retention ring 12" for the present bone screw retention mechanism. The retention ring 12" is shaped to provide several springs that extend radially into the bone screw bore. The retention ring 12" is formed by a preferably, but not necessarily, continuous ring or body 20" of a biocompatible and elastic material so as to provide a spring force when deformed. Preferably, the retention ring 12" is formed of nitinol (a nickel titanium alloy) since nitinol alloys exhibit shape memory and elasticity. The body 20" of the retention ring 12" has three waves or curves 24a", 24b", 24c" that each define a spring which extends radially into the bone screw bore of the spinal implant, while the connecting portions 22a", 22b", 22c" extend into the retention channel of the bone screw bore. In this manner, the retention ring 12" is thus trapped or retained in the retention channel while the springs 24a", 24b", 24c" extend into the bone screw bore. The springs 24a", 24b", 24c" are preferably, but not necessarily, evenly spaced about the ring 12" and create an opening in the middle thereof in order to allow the introduction of a bone screw. The other features, structures, and/or variations discussed with regard to the retention ring 12 not discussed in this paragraph applies to the retention ring 12" and is hereby incorporated herein by reference.

Figure 9:
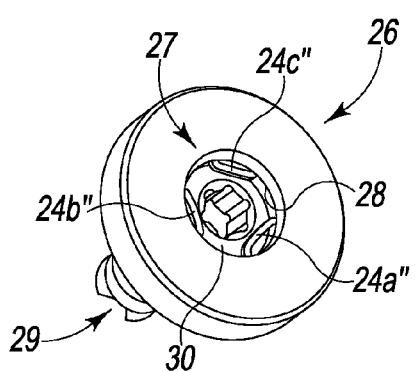
FIG. 9 is an isometric view of the mock up bone screw hole of FIG. 3 having the present bone screw retention mechanism using the resilient retention ring of FIG. 8.

FIG. 9 illustrates the mock up 26 of a bone screw bore of a spinal implant incorporating the present bone screw retention mechanism having a bone screw 29 captured by the present bone screw retention mechanism. The springs 24a", 24b", 24c" elastically deform in the radial direction in order to spread outwardly and into the retention channel when the head of the bone screw 29 is forced down and between the springs 24a", 24b", 24c". Interaction and/or functionality between the bone screw head 30 and the springs 24a", 24b", 24c" of the ring 12" may be enabled, provided and/or controlled through appropriate interface geometry of the bone screw head and/or the springs. In FIG. 9 the radiused underside of the head 30 of the bone screw 29 interacts with the springs 24a", 24b", 24c" of the ring 12" to spread the springs 24a", 24b", 24c" open. Other geometries, configurations, features, structure and/or structures of the bone screw/bone screw head and/or springs are contemplated. Thereafter, when the head clears the springs 24a", 24b", 24c", the springs 24a", 24b", 24c" elastically spring outward to block egress of the head from the bone screw bore. Particularly, the springs 24a", 24b", 24c" extend over and/or about the top of the head of the bone screw bore. The interaction and/or functionality between the top of the head 30 and the springs 24a", 24b", 24c" may be enabled, provided and/or controlled through appropriate interface geometry of the top of the bone screw head and/or the springs. In FIG. 9, since the top of the head is flat, it cannot spread the curved springs 24a", 24b", 24c" and thus is captured in the bone screw bore. Other geometries and/or configurations of the top of the bone screw head and/or springs are contemplated.

Figure 10:
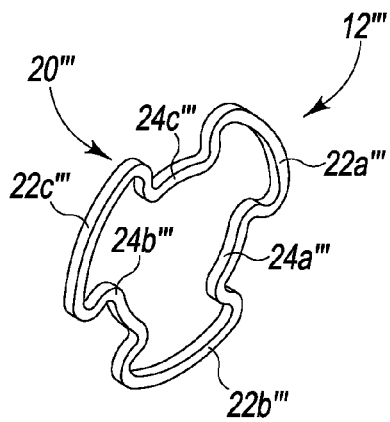
FIG. 10 is an isometric view of another embodiment of a resilient retention ring for the present bone screw retention mechanism.

Referring to FIG. 10 there is shown another embodiment of a retention ring 12''' for the present bone screw retention mechanism. The retention ring 12''' is shaped to provide several springs that extend radially into the bone screw bore. The retention ring 12''' is formed by a preferably, but not necessarily, continuous ring or body 20''' of a biocompatible and elastic material so as to provide a spring force when deformed. Preferably, the retention ring 12''' is formed of nitinol (a nickel titanium alloy) since nitinol alloys exhibit shape memory and elasticity. The body 20''' of the retention ring 12''' has three waves or curves 24a''', 24b''', 24c''' that each define a spring which extends radially into the bone screw bore of the spinal implant, while the connecting portions 22a''', 22b''', 22c''' extend into the retention channel of the bone screw bore. In this manner, the retention ring 12''' is thus trapped or retained in the retention channel while the springs 24a''', 24b''', 24c''' extend into the bone screw bore. The springs 24a''', 24b''', 24c''' are preferably, but not necessarily, evenly spaced about the ring 12''' and create an opening in the middle thereof in order to allow the introduction of a bone screw. The other features, structures, and/or variations discussed with regard to the retention ring 12 not discussed in this paragraph applies to the retention ring 12''' and is hereby incorporated herein by reference.

Figure 11:
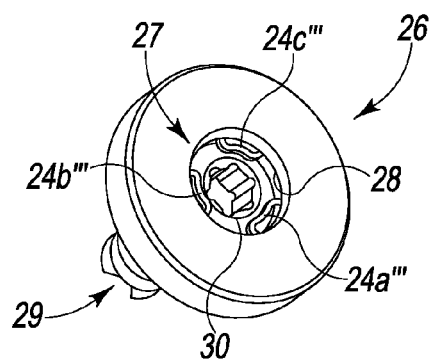
FIG. 11 is an isometric view of the mock up bone screw hole of FIG. 3 having the present bone screw retention mechanism using the resilient retention ring of FIG. 10.

FIG. 11 illustrates the mock up 26 of a bone screw bore of a spinal implant incorporating the present bone screw retention mechanism having a bone screw 29 captured by the present bone screw retention mechanism. The springs 24a''', 24b''', 24c''' elastically deform in the radial direction in order to spread outwardly and into the retention channel when the head of the bone screw 29 is forced down and between the springs 24a''', 24b''', 24c'''. Interaction and/or functionality between the bone screw head 30 and the springs 24a''', 24b''', 24c''' of the ring 12''' may be enabled, provided and/or controlled through appropriate interface geometry of the bone screw head and/or the springs. In FIG. 11 the radiused underside of the head 30 of the bone screw 29 interacts with the springs 24a''', 24b''', 24c''' of the ring 12''' to spread the springs 24a''', 24b''', 24c''' open. Other geometries, configurations, features, structure and/or structures of the bone screw/bone screw head and/or springs are contemplated. Thereafter, when the head clears the springs 24a''', 24b''', 24c''', the springs 24a''', 24b''', 24c''' elastically spring outward to block egress of the head from the bone screw bore. Particularly, the springs 24a''', 24b''', 24c''' extend over and/or about the top of the head of the bone screw bore. The interaction and/or functionality between the top of the head 30 and the springs 24a''', 24b''', 24c''' may be enabled, provided and/or controlled through appropriate interface geometry of the top of the bone screw head and/or the springs. In FIG. 11, since the top of the head is flat, it cannot spread the curved springs 24a''', 24b''', 24c''' and thus is captured in the bone screw bore. Other geometries and/or configurations of the top of the bone screw head and/or springs are contemplated.

While the retention rings/bands shown herein are all continuous, a retention ring may include a gap or be formed by several individual springs strategically situated in one or more retention channels. Moreover, the retention ring is preferably, but not necessarily, formed by a wire. The wire (or other spring material) may be round, rectangular, sheet-like or otherwise. The outer surface of the retention ring may be contoured (e.g. curves and/or flats) to provide an appropriate interface geometry. The retention channel of the bone screw may have a contour complementary to the outer surface and/or cross section of the retention ring or otherwise have appropriate interface geometry.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. A spinal implant comprising:
   a body;
   a bore extending through the body and defining a bore wall; and
   a band situated in the bore wall, the band comprising:
      three resilient curved portions that extend radially inward into the bore and allow a head of a bone screw to pass there through but prevent the head of the bone screw from exiting there from; and
      a plurality of connecting portions, each disposed between adjacent resilient curved portions, wherein each connecting portion includes a pair of curved segments being concave in shape relative to an interior of the band and having a convex portion disposed therebetween;
   wherein the resilient curved portions are equally spaced about the band.

2. The spinal implant of claim 1, wherein the band comprises a continuous closed curved structure.

3. The spinal implant of claim 2, wherein the bore wall includes a groove, the band situated in the groove.

4. The spinal implant of claim 2, wherein the entire band is composed of a resilient material.

5. The spinal implant of claim 4, wherein the resilient material is nitinol.

6. A spinal implant comprising:
   a body;
   a bore extending through the body and defining a bore wall;
   a channel disposed in the bore wall; and
   a band situated in the channel, the band comprising three resilient curved portions that extend radially inward into the bore to form springs and allow a head of a bone screw to pass there through but prevent the head of the bone screw from exiting there from;
   wherein the band includes a plurality of connecting portions, each disposed between adjacent resilient curved portions, wherein each connecting portion includes a pair of curved segments being concave in shape relative to an interior of the band and having a convex portion disposed therebetween;
   wherein the three resilient curved portions are equally spaced about the band.

7. The spinal implant of claim 6, wherein the band comprises a continuous closed curved structure.

8. The spinal implant of claim 7, wherein the entire band is composed of a resilient material.

9. The spinal implant of claim 8, wherein the resilient material is nitinol.

* * * * *